(12) United States Patent
Watano et al.

(10) Patent No.: US 6,225,809 B1
(45) Date of Patent: May 1, 2001

(54) STATIC ELECTRICITY MEASURING SYSTEM

(75) Inventors: Satoru Watano, Osaka; Katsuyuki Kamihashi, Atsugi; Teruo Suzuki, Tokyo; Kenshi Suzuki, Chiba; Yasuo Morikawa, Niiza, all of (JP)

(73) Assignee: Kasuga Denki, Inc., Tokyo (JP)

( * ) Notice: Subject to any disclaimer, the term of this patent is extended or adjusted under 35 U.S.C. 154(b) by 0 days.

(21) Appl. No.: 09/276,467

(22) Filed: Mar. 25, 1999

(30) Foreign Application Priority Data

Apr. 16, 1998 (JP) .................................................. 10-106793

(51) Int. Cl.$^7$ .................................................. G01N 27/62
(52) U.S. Cl. ................................................................ 324/464
(58) Field of Search ........................................ 324/454, 452, 324/457, 464, 156, 455, 72, 686, 663, 688, 204, 71.1, 96, 750, 72.5

(56) References Cited

U.S. PATENT DOCUMENTS 4,139,813 * 2/1979 Shaffer .................................... 324/32

FOREIGN PATENT DOCUMENTS

| 5-126883 | 5/1993 | (JP) . |
| 7-1291 | 1/1995 | (JP) . |
| 10-62471 | 3/1998 | (JP) . |
| 10062471 | * 3/1998 | (JP) .............................. G01R/29/24 |

OTHER PUBLICATIONS

Watano, Article entitled "The On–line Monitoring of the Electrostatic Field Strength . . .", Oct., 1997, pp. 778–784.*
Title: "Development of Electrostatic–Field Detecting System for Powder Clouds" by Teruo Suzuki et al, all of Kasuga Denki Inc. Issued in Oct. 1992., pp. 541–544 (with English Abstract).
Title: "A safety Evaluating Test of Electrostatic–Field Sensing System for Powder–Cloud in a Fluidized Drier (I)" by Yasuyuki Tabata et al. Issued in Sep., 1993., pp. 443–446 (with English Abstract).
Title: "Detection of Electrostatic Field Diverged from Charged Cloud Formed by Fluidized Particles" by Yasuyuki Tabata et al. Issued in 1994., pp. 143–152 (with English Abstract).
Title: "Effect of Humidity on Electrostatic Charging on Powders in Pneumatic Transport" by Tsutomu Kodama et al. Issued in Oct. 1995., pp. 221–224 (with English Abstract).
Title: "The On–line Monitoring of the Electrostatic Field Strength in Fluidized Bed Granulation and Drying Using a Newly Developed Electrostatic Field Detecting System" by Satoru Watano et al. Issued Oct. 1997., pp. 778–784 (with English Abstract).
Title: "On–line Monitoring of Electrostatic Field Strength in Powder Pneumatic Transportation Process Using Newly Developed Electrostatic Field Detecting System" by Teruo Suzuki et al. Issued in 1998., pp. 846–855 (with English Abstract).

* cited by examiner

*Primary Examiner*—Safet Metjahic
*Assistant Examiner*—E P LeRoux
(74) *Attorney, Agent, or Firm*—Oblon, Spivak, McClelland, Maier & Neustadt, P.C.

(57) ABSTRACT

A static electricity measuring system including a probe, a measuring device, and a calibration device. The probe includes a sensor which detects an electric field and outputs signals representing the detected electric field. The measuring device measures static electricity on the basis of the signals output from the sensor. The calibration device generates a reference electric field. The measuring device is adjusted when the sensor detects the reference electric field produced by the calibration device.

37 Claims, 17 Drawing Sheets

STATIC ELECTRICITY MEASURING SYSTEM

CROSS-REFERENCE TO RELATED APPLICATIONS

The present application claims priority under 35 U.S.C. §119 to Japanese Patent Application No. 10-106,793, filed Apr. 16, 1998, entitled "Static Electricity Measuring Apparatus." The contents of that application are incorporated herein by reference in their entirety.

BACKGROUND OF THE INVENTION

1. Field of the Invention

The present invention relates to a static electricity measuring system.

2. Description of the Related Art

Static electricity measuring apparatuses are disclosed in Japanese Unexamined Patent Publication (Kokai) 5-126,883 (hereinafter referred to as the "'883 publication"), entitled "Correcting Apparatus For Powder Electric Charge Measuring Device"; and Japanese Examined Patent Publication (Kokoku) 7-1,291 (hereinafter referred to as the "'291 publication"), entitled "Apparatus For Detecting Electric Potential Of Charged Powder And Apparatus For Controlling Charging." The contents of these applications are incorporated herein by reference in their entirety.

The '883 publication discloses a correcting apparatus for correcting a measuring error in a measuring device when electric charge of conductive powder for a copying machine is measured. In this apparatus, the amount of electric charge of the toner is measured by a suction type Faraday cage when the voltage is applied to the toner. The measured value is corrected by comparing the measured value with a reference value of a reference Faraday cage.

In this apparatus, however, toner sample is removed from the copying machine and subsequently the amount of electric charge of the toner is measured. Thus, the amount of electric charge of the toner cannot be measured in the copying machine in real time.

The '291 publication discloses an apparatus for detecting electric potential of charged powder flowing in a fluid dryer. In this apparatus, an electric potential detecting unit is attached to an outer side wall of the dryer. The detecting unit detects the electric potential through a detecting hole which faces a window provided in the outer side wall of the dryer. In order to prevent the flowing powder from entering the inside of the detecting unit through the detecting hole, air is supplied between the window and the detecting hole to form an air layer therebetween which serves as a barrier.

In this apparatus, however, the entrance of the powder to the detecting unit. is not effectively prevented. Accordingly, the apparatus does not precisely detect electric potential of the charged flowing powder.

SUMMARY OF THE INVENTION

An object of the present invention is to provide a static electricity measuring system which precisely detects static electricity of powder, solvent, gas or the like without sampling them.

This object is achieved according to the present invention by providing a static electricity measuring system which includes a probe, a measuring device and a calibration device. The probe includes a sensor which detects an electric field and outputs signals representing the detected electric field. The measuring device measures static electricity on the basis of the signals output from the sensor. The calibration device generates a reference electric field. The measuring device is adjusted when the sensor detects the reference electric field produced by the calibration device.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DETAILED DESCRIPTION OF THE PREFERRED EMBODIMENTS

Figure 1:
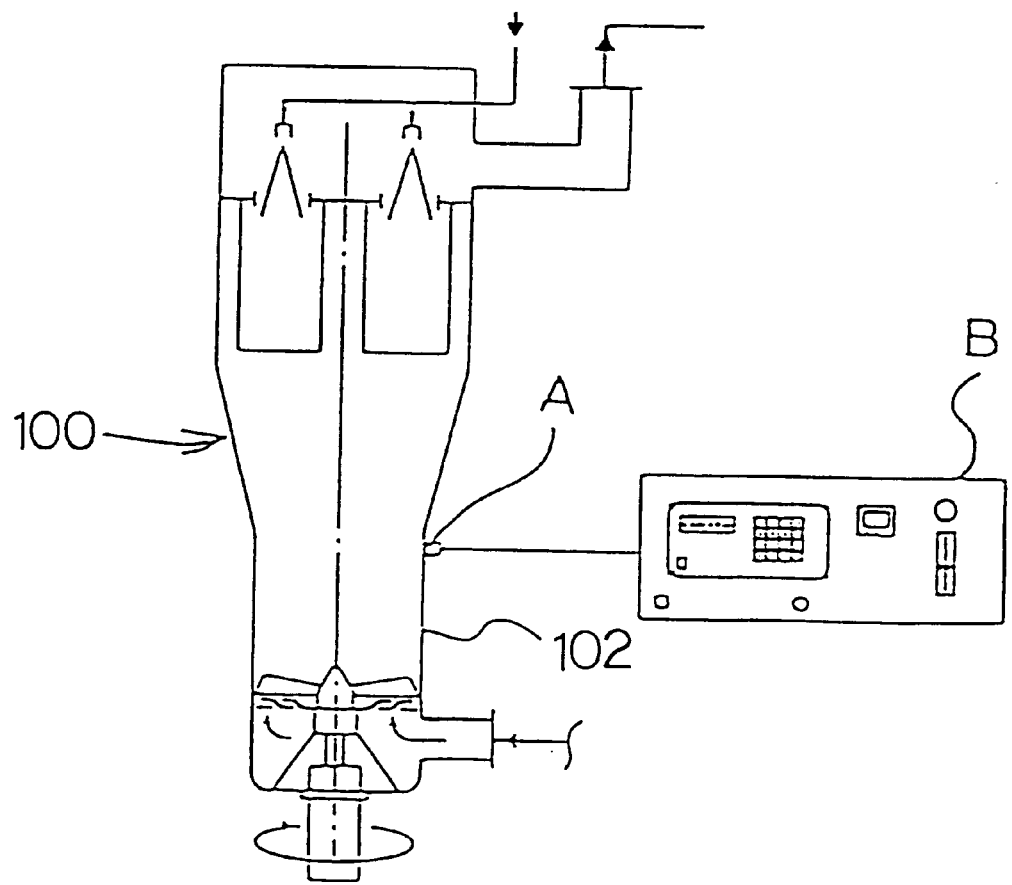
FIG. 1 shows a static electricity measuring apparatus of a static electricity measuring system according to the present invention which is attached to a fluid dryer.

The preferred embodiments will now be described with reference to the accompanying drawings, wherein like reference numerals designate corresponding or identical elements throughout the various drawings.

FIG. 1 shows a static electricity measuring apparatus which is attached to a fluid dryer 100. Referring to FIG. 1, a probe (A) is provided on a side surface 102 of a fluid dryer 100. The forward portion of the probe (A) is inserted in the fluid dryer 100 through a hole provided in the fluid dryer 100. The components of the fluid dryer 100 such as the illustrated fan are not critical to an understanding of the invention and a description thereof is omitted for brevity. The probe (A) is connected to a measuring device (B). The probe (A) detects static electricity of charged particles which flow inside the fluid dryer 100. The measuring device (B) displays the detected static electricity.

Figure 2:
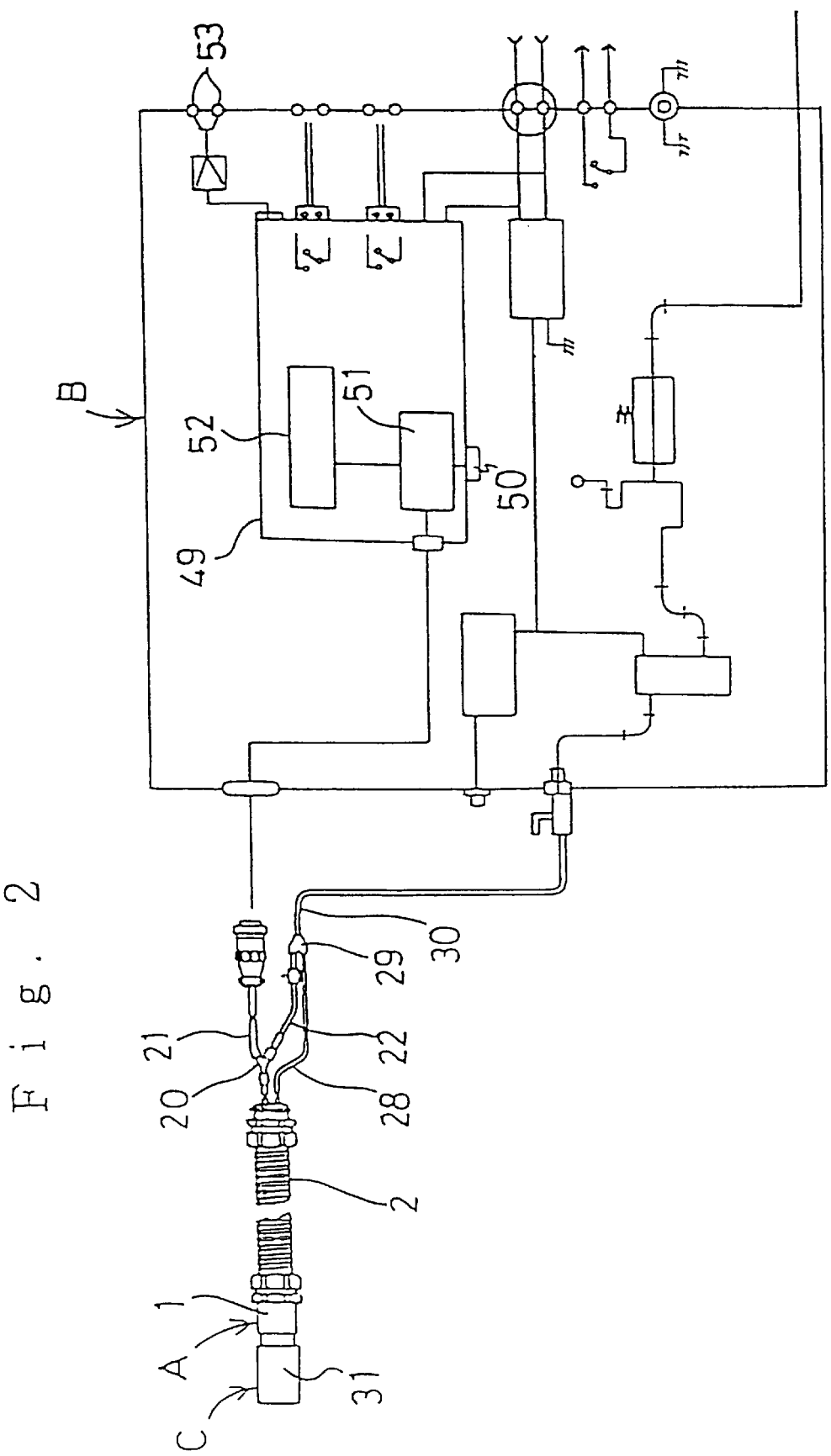
FIG. 2 illustrates the static electricity measuring system according to the first embodiment of the present invention.

FIG. 2 shows a static electricity measuring system according to a first embodiment of the present invention. The embodiment of FIG. 2 may be applied to the dryer of FIG. 1. The system includes the probe (A), the measuring device (B), and a calibration device (C). The calibration device (C) generates a reference electric field, for example, a reference electrostatic field. The calibration device (C) is attached to the front end of the probe (A) when the measuring device (B) is adjusted, and detached from the probe (A) when the probe (A) detects static electricity of charged particles which flows inside the fluid dryer 100 (FIG. 1).

Figure 3:
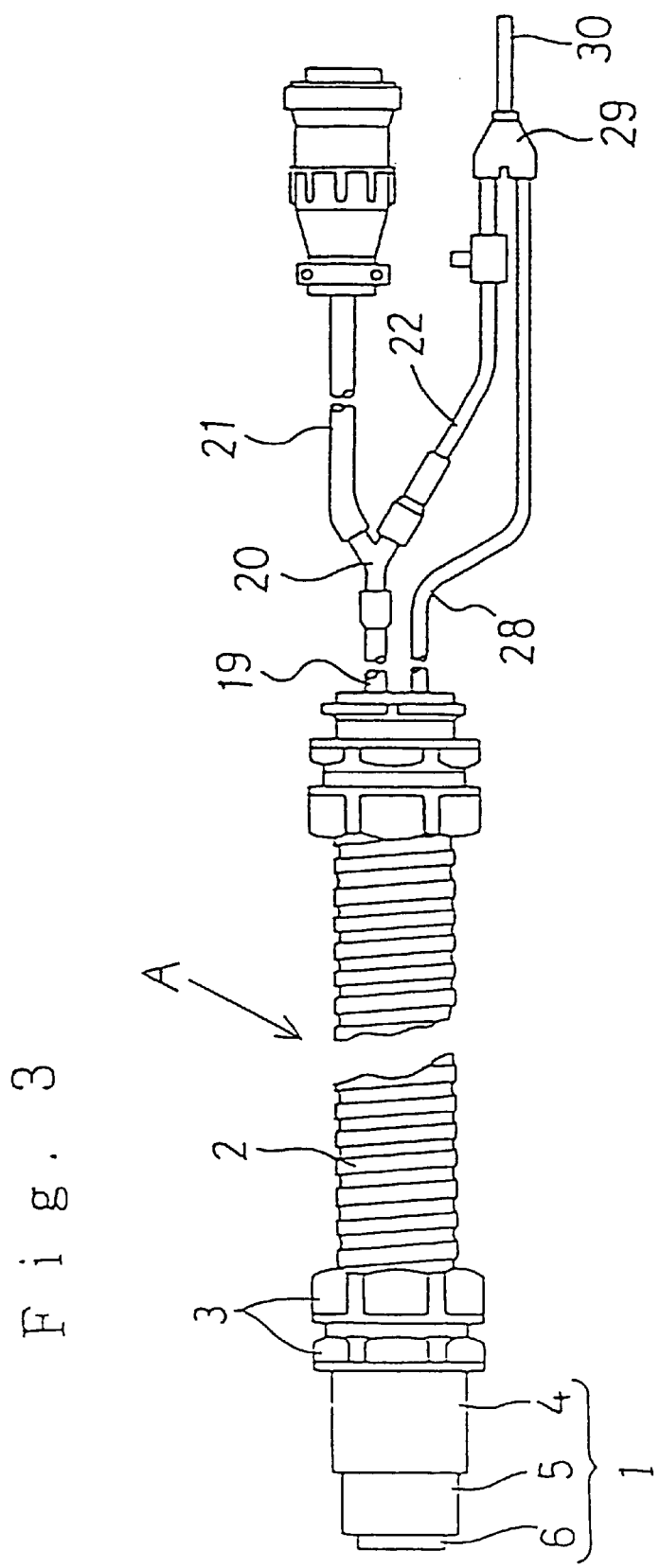
FIG. 3 is a side view of a probe of the static electricity measuring system according to the first embodiment of the present invention.
Figure 4:
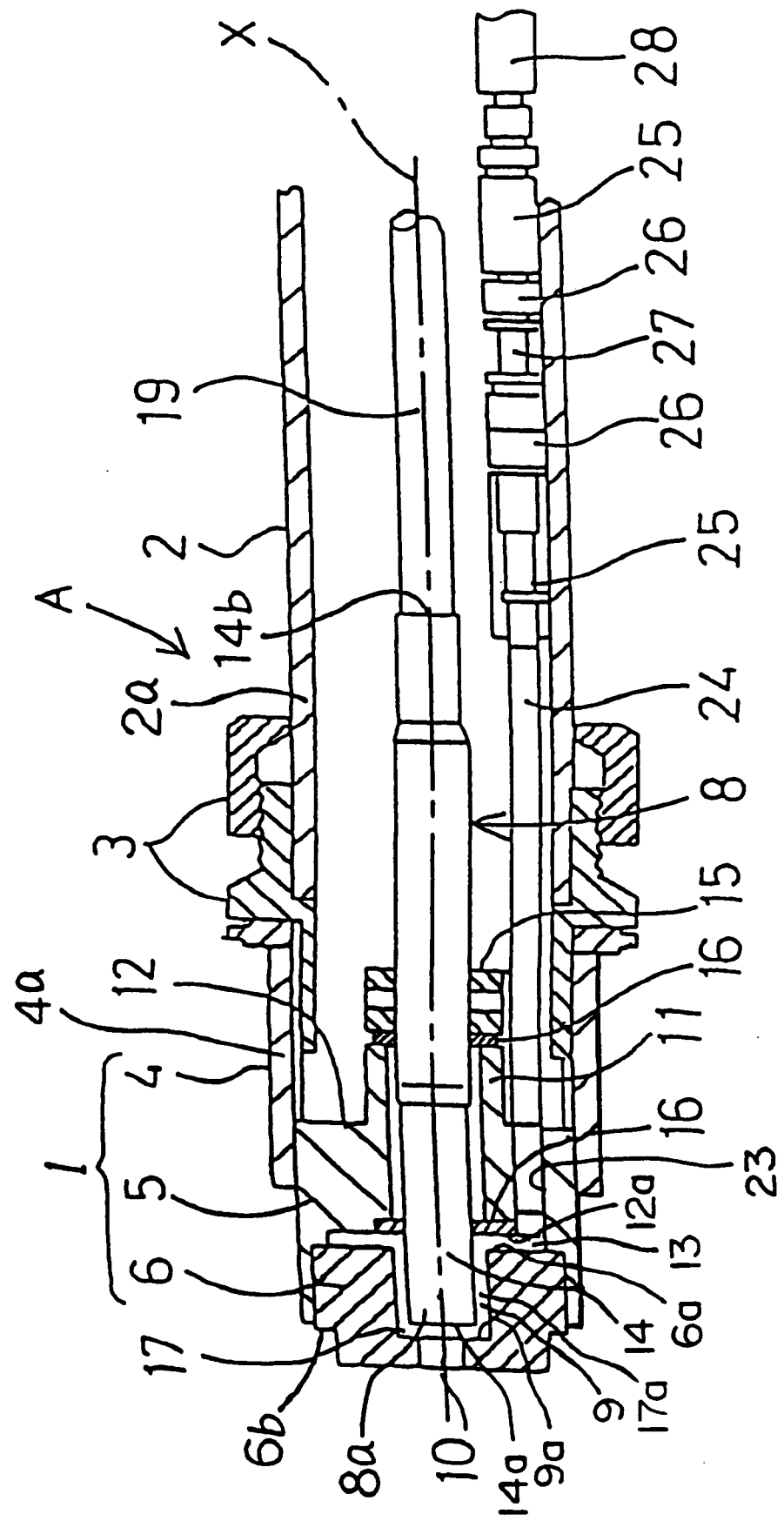
FIG. 4 is a cross-sectional view of the probe of the static electricity measuring system according to the first embodiment of the present invention.

FIG. 3 shows a side view of the probe (A) and FIG. 4 shows a cross-sectional view of the probe (A) of the static electricity measuring system according to the first embodiment of the present invention. Referring to FIGS. 3 and 4, the probe (A) includes a flexible tube 2 and a probe case 1 which is connected to a front end (2a) of the flexible tube 2 via a connecting nut 3. The probe case 1 is directed to any position by bending the flexible tube 2.

The probe case 1 includes a rear cylinder 4 which is connected to the front end (2a) of the flexible tube 2 via the connecting nut 3; a front cylinder 5 which is inserted into and connected to a front end (4a) of the rear cylinder 4; and a cylindrical front cap 6 which closes a front opening of the front cylinder 5. The probe case 1 contains a sensor 8 for detecting an electric field. In this embodiment, the sensor 8 detects, for example, an electrostatic field. The rear cylinder 4, the front cylinder 5, and the front cap 6 are made from, for example, metal. For example, stainless steel, Inconel, or nickel alloy can be used as the metal according to the atmosphere around the probe case 1. As the nickel alloy, nickel-molybdenum alloy, nickel-chromium-molybdenum alloy, or nickel-chromium iron can be used. For example, as the nickel-chromium-molybdenum alloy, "HASTELLOY" (trademark) which has a composition of Ni—22Cr—13Mo—4Fe—3W—0.10C and which is manufactured by Mitsubishi Material Co. can be used.

The front cap 6 has a cylindrical concave portion 9 and a purge hole 10 which extends through the front cap 6 and opens toward the concave portion 9. For example, the purge hole 10 has a diameter of around 7 mm and a length of approximately 5 to 6 mm. The front cap 6, the cylindrical concave portion 9, and a purge hole 10 have a common center axis (X). The front cap 6 further has an annular step portion 6b on the front side of the front cap 6. The front cylinder 5 has an inner cylinder 11 which is connected to the front cylinder 5 by an annular connecting portion 12. A front surface 12a of the annular connecting portion 12 and a rear surface 6a of the front cap 6 forms a gap 13 therebetween.

Figure 5:
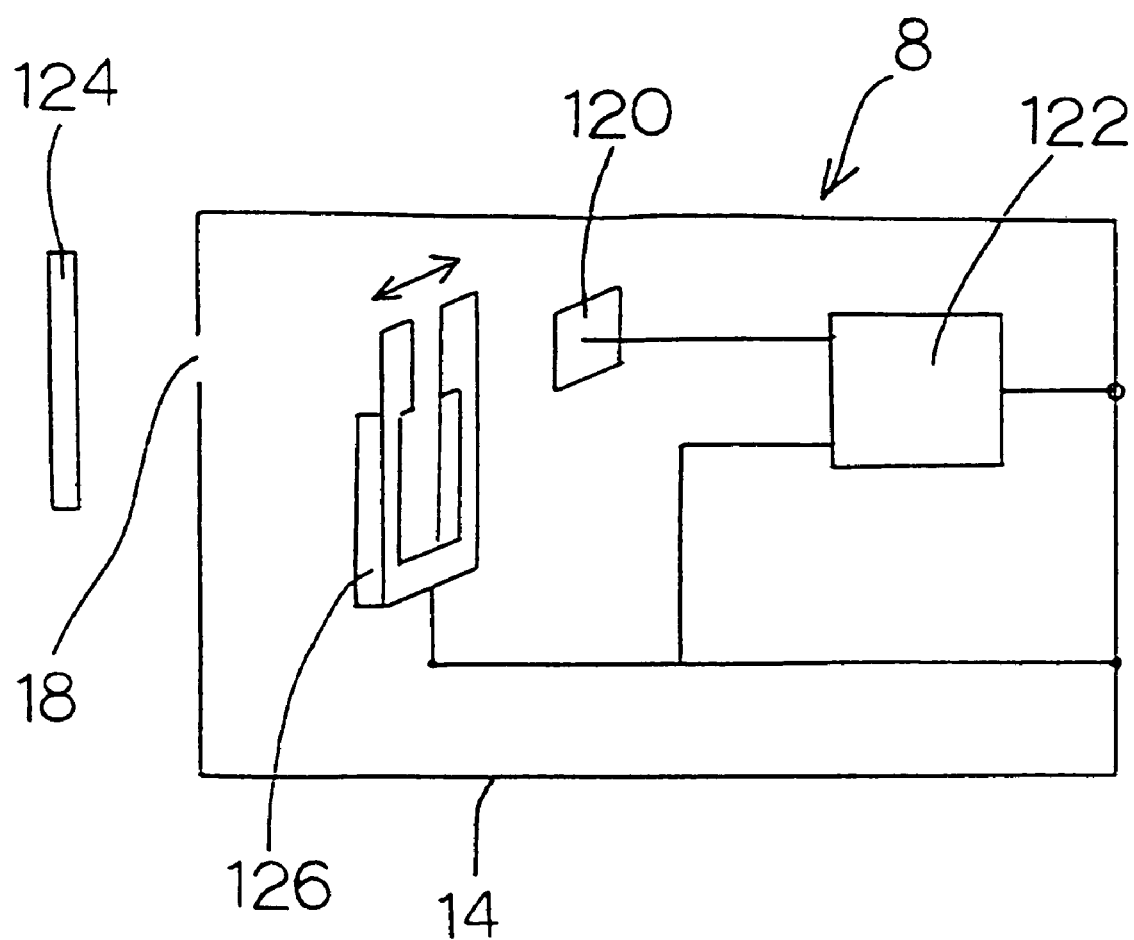
FIG. 5 is a schematic illustration of a sensor contained in the probe of the static electricity measuring system according to the present invention.

The sensor 8 is, for example, a vibration capacity or chopper type sensor which may be known devises. As the sensor 8, for example, Electrostatic Voltmeter Probe Model 1017 E which is manufactured by Monroe Electronics Inc. can be used. Referring to FIG. 5, the sensor 8 includes a cylindrical sensor case 14 which contains therein a detecting electrode 120 and a static electricity detecting circuit 122 which is connected to the detecting electrode 120. The sensor case 14 is made from, for example, metal. A capacitance between an object 124 to be measured and the detecting electrode 122 through a detecting hole 18 is cyclicly changed utilizing, for example, mechanical means such as a piezoelectric tuning fork 126 contained in the cylindrical sensor case 14. Accordingly, a cyclicly alternate electric charge is induced in the detecting electrode 120. The cyclicly alternate electric charge generates current, which is converted to voltage by the static electricity detecting circuit 122. Accordingly, the sensor 8 outputs voltage as output signals. In another example, the sensor 8 may output current as output signals.

Figure 6:
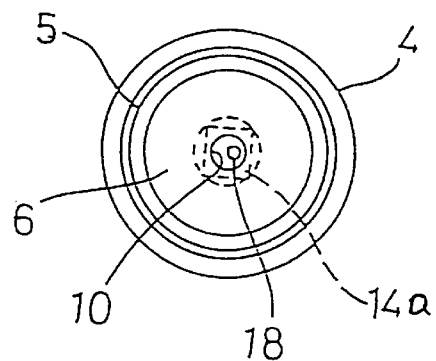
FIG. 6 is a top plan view of the probe of the static electricity measuring system according to the first embodiment of the present invention.

Referring to FIGS. 3 and 4, the sensor 8 is arranged in and connected to the inner cylinder 11 via a connecting metal member 15. Gaskets 16 are provided at front and rear ends of the inner cylinder 11 to seal gaps between the sensor 8 and the inner cylinder 11. The front portion 8a of the sensor 8 is arranged in the cylindrical concave portion 9 of the front cap 6 to form a gap 17 between the inner surface 9a of the concave portion 9 and a front surface 14a of the sensor case 14 and to form a gap 17a between an inner circumferential surface of the concave portion 9 and an outer circumferential surface of the sensor case 14. The gap 13 communicates with the purge hole 10 via the gaps 17a and 17. A front surface 14a of the sensor case 14 has the detecting hole 18 (see FIG. 6) which has a diameter smaller than that of the purge hole 10. The sensor 8 is arranged in the probe case 1 such that the detecting hole 18 is positioned in the vicinity of the purge hole 10. The sensor 8 detects the electric field via the detecting hole 18 and the air purge hole 10.

One end of a hose 19 is connected to a rear end 14b of the sensor case 14. The other end of the hose 19 is connected to a cable 21 and an air hose 22 via a dividing joint 20 at the outside of the flexible tube 2. The cable 21 connects the static electricity detecting circuit 122 (see FIG. 5) in the sensor 8 to the measuring device (B)(see FIG. 2).

As shown in FIG. 4, the annular connecting portion 12 has a through hole 23 into which an air supplying hose 24 is introduced. In the flexible tube 2, the air supplying hose 24 is connected to an air hose 28 via sockets 25, joints 26, and a flexible tube 27. The air hoses 22 and 28 are connected to a common air hose 30 via a joint 29. Accordingly, air is supplied to the inside of the sensor 8 via the air hose 22 and to the gaps (13, 17a and 17) via the air hose 28. The common air hose 30 is connected to the measuring device (B) which has a controller for controlling the air supply to the common air hose 30 (see FIG. 2).

The air supplied to the inside of the sensor 8 is discharged from the detecting hole 18, and the air supplied to the gaps (13, 17a and 17) is discharged from the air purge hole 10. In the present embodiment, the discharging air pressure at the detecting hole 18 is higher than that at the air purge hole 10. Accordingly, air supplied to the gaps (13, 17a and 17) does not enter the inside of the sensor 8 through the detecting hole 18. Particles and dust are prevented from entering the inside of the probe (A), because air which is discharged from the detecting hole 18 and which is supplied to the gaps (13, 17a and 17) is discharged from the air purge hole 10. Further, since the air supplied to the gap 13 is discharged from the air purge hole 10 after passing through the gaps (17a and 17), particles and dust are prevented from adhering to the outside surface of the sensor case 14. Furthermore, since air is discharged from the detecting hole 18 of the sensor 8, particles and dust are prevented from entering the inside of the sensor 8.

In this embodiment, the front portion 8a of the sensor 8 is inserted in the cylindrical concave portion 9 formed in the front cap 6. Accordingly, even though the sensor 8 is arranged in the probe case 1, the sensor 8 can maintain its detecting performance.

Figure 7:
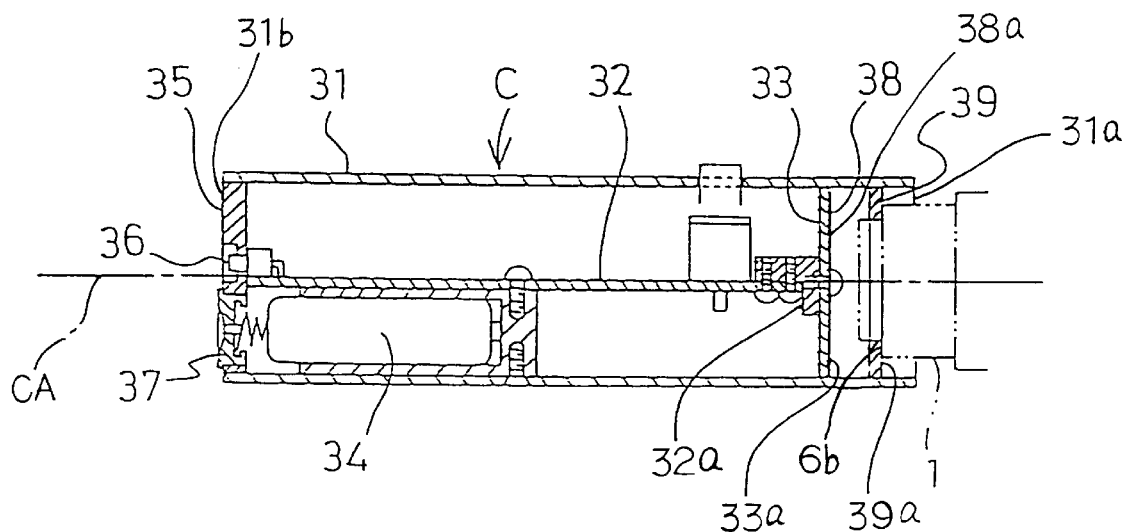
FIG. 7 is a cross-sectional view of a calibration device of the static electricity measuring system according to the first embodiment of the present invention.
Figure 8:
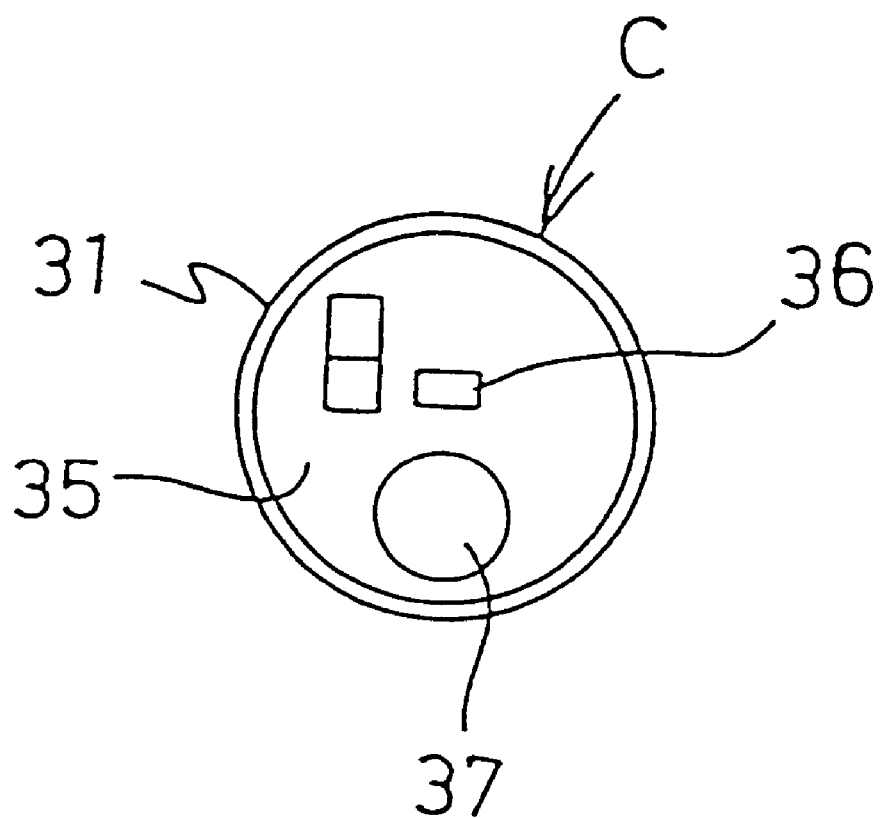
FIG. 8 is a side view of the calibration device of the static electricity measuring system according to the first embodiment of the present invention.

Referring to FIGS. 7 and 8, the calibration device (C) includes a cylindrical case 31. The cylindrical case 31 contains a circuit board 32, printed circuit board 33, a power source such as a battery 34, and a rear lid 35. The circuit board 32 includes a D.C. high voltage generating circuit (D) (see FIG. 8) and is arranged along a center axis (CA) of the cylindrical case 31. The printed circuit board 33 is arranged in the vicinity of a front opening 31a of the cylindrical case 31 and fixed to the front end 32a of the circuit board 32 to be substantially perpendicular to the center axis (CA). The rear lid 35 closes a rear opening 31b of the cylindrical case 31 and includes a power switch 36 and a battery cover 37. A copper foil 38 which serves as an electromagnetic field radiator or a metal plate is provided on a substantially entire front surface 33a of the printed circuit board 33. The cylindrical case 31 further includes a stopper 39 which is provided between the copper foil 38 and a front opening 31a of the cylindrical case 31. The stopper 39 has a front surface 39a which is substantially parallel to a front surface 38a of the copper foil 38.

Figure 9:
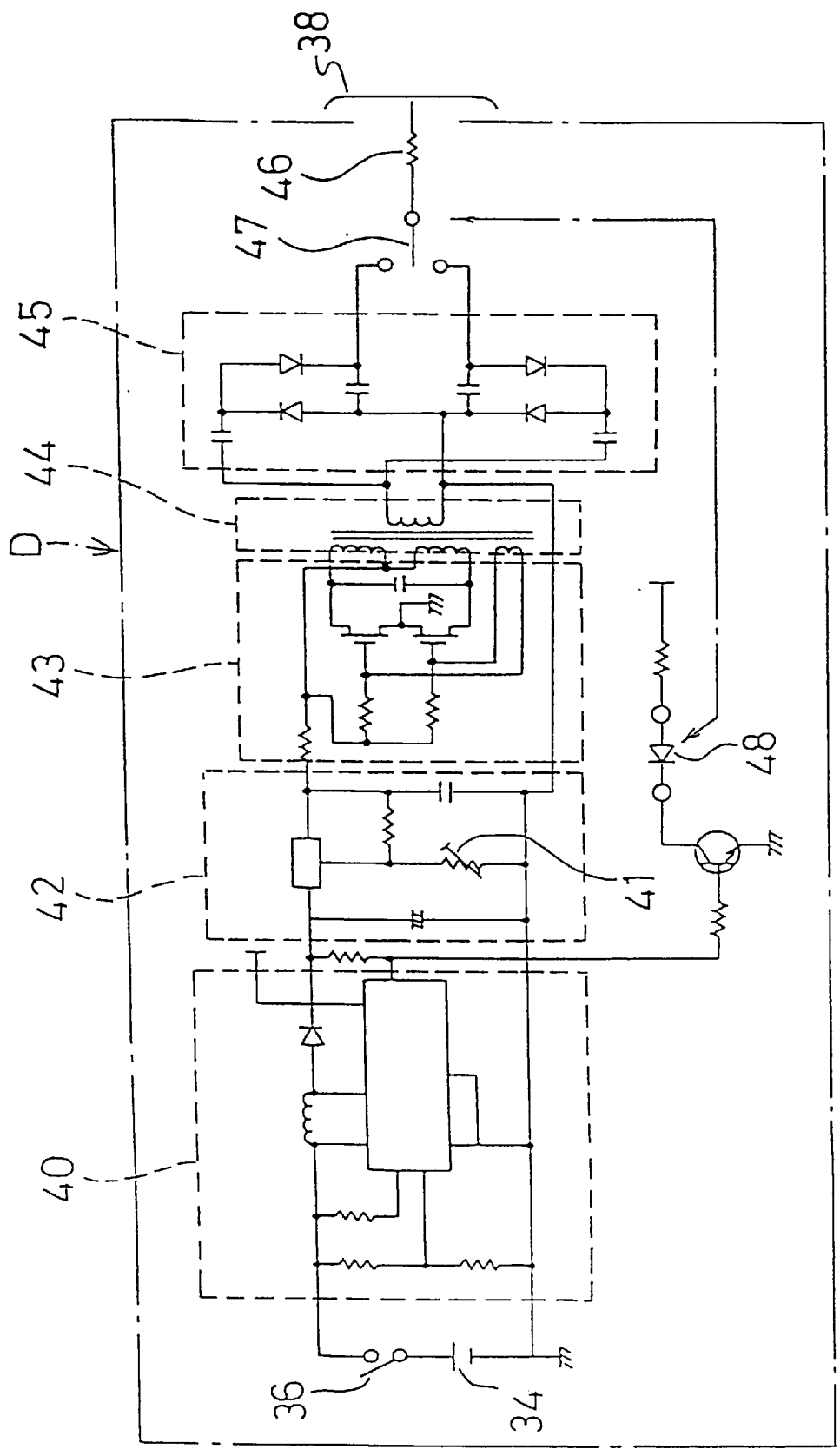
FIG. 9 illustrates a D.C. high voltage generating circuit which is included in the calibration device.

Referring to FIG. 9, the D.C. high voltage generating circuit (D) includes a boosting circuit (a DC/DC converter) 40, a constant-voltage circuit 42, an oscillation driving circuit 43, a high-frequency transformer 44, a rectifier circuit 45, a polarity changeover switch 47, and an operation checking lamp 48 which may be implemented as a light emitting diode ("LED"). The boosting circuit 40 boosts the DC voltage of the power source battery 34 (for example, from 1.5V to 5V). The constant-voltage circuit 42 sets the boosted voltage at a constant voltage which is within a predetermined range (for example, 1.5V to 4V) determined by a variable resistor 41. The oscillation driving circuit 43 oscillates by the constant voltage. The high-frequency transformer 44 boosts the high-frequency voltage output from the oscillation driving circuit 43. The rectifier circuit 45 rectifies and amplifies the secondary voltage of the high-frequency transformer 44. The polarity changeover switch 47 switches the polarity of the DC high-voltage which is applied to the copper foil 38 via the rectifier circuit 45 and a register 46.

As shown in FIGS. 2 and 7, when the measuring device (B) is adjusted or calibrated, the probe case 1 of the probe (A) is introduced into the cylindrical case 31 of the calibration device (C) through the front opening 31a such that the annular step portion 6b of the probe case 1 engages with the stopper 39. Accordingly, the sensor 8 (see FIG. 4) is positioned with respect to the copper foil 38 such that the distance between the sensor 8 and the copper foil 38 is constant.

When the power switch 36 of the calibration device (C) is turned on, constant DC high-voltage which has a polarity set by the polarity changeover switch 47 is applied to the copper foil 38. Namely, the copper foil 38 is a simulated charged object which is charged with constant high-voltage. Accordingly, the calibration device (C) generates a reference electric field, for example, a reference electrostatic field. In the measuring device (B) shown in FIG. 2, the signals output from the probe (A) are displayed in a display 49 after being amplified by an amplifier 51. An amplification factor of the amplifier 51 is adjusted by turning a sensitivity knob 50 of the display 49 to show characteristics of static electricity, for example, electric field, voltage, or electric charge of static electricity.

After the measuring device (B) is adjusted or calibrated, the calibration device (C) is detached from the probe (A). Then, the probe (A) is attached to the fluid drier 70 as shown in FIG. 1 to measure static electricity of the charged particles flowing inside the fluid dryer 70. Accordingly, electric field, voltage, or an amount of electric charge can be precisely measured while the charged particles flow inside the fluid drier 70. The measuring device (B) has an output terminal 53 to be connected to, for example, a personal computer in order to process the data output from the measuring device (B). The measuring device (B) can be easily adjusted or calibrated at any time, because the calibration device (C) is detachable and portable.

Accordingly, according to the first embodiment of the present invention, the static electricity can be precisely measured while the charged particles flow inside the fluid drier 70, because the sensor 8 detects the electric field, for example, electrostatic field, for measuring the static electricity. Further, particles and dust are prevented from entering the inside of the sensor 8 and adhering to the outside surface of the sensor case 14. Accordingly, the static electricity can be precisely measured for a long period of time. Furthermore, the sensor 8 can maintain its detecting performance even though the sensor 8 is arranged in the probe case 1. Furthermore, the measuring device (B) can be easily adjusted or calibrated at any time.

Figure 10:
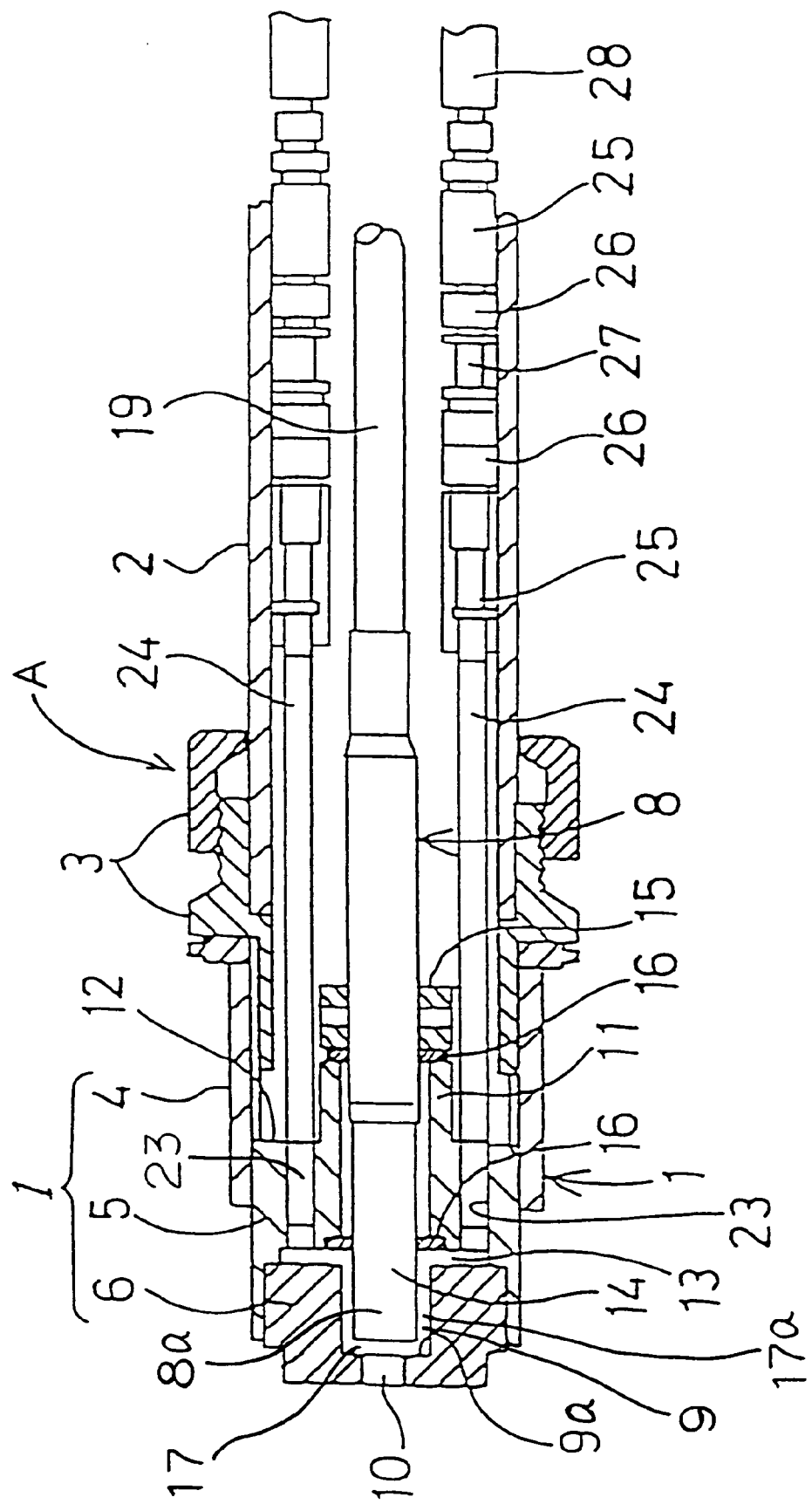
FIG. 10 is a cross-sectional view of a probe of a static electricity measuring system according to a second embodiment of the present invention.

FIG. 10 is a cross-sectional view of a probe (A) according to a second embodiment of the present invention. In this embodiment, two or more of the air supplying are utilized. While FIG. 10 illustrates two of the air supply hoses 24, any number may be used including two, three, four, five, six, or more. In order to reduce clutter in FIG. 10, a second set of reference numerals has not been added to each of the elements of the second air supplying device. Referring to FIG. 10, the probe (A) has plural through holes 23 and plural air supplying hoses 24 which are arranged substantially in parallel to each other. Preferably, the plural through holes 23 are positioned such that the distances between the through holes 23 along the circumferential direction of the annular connecting portion 12 are substantially equal to each other. According to the second embodiment, air is more equally distributed around the front portion 8a of the sensor 8. Accordingly, particles and dust are prevented from adhering to the outside surface of the sensor case 14 more effectively.

Figure 11:
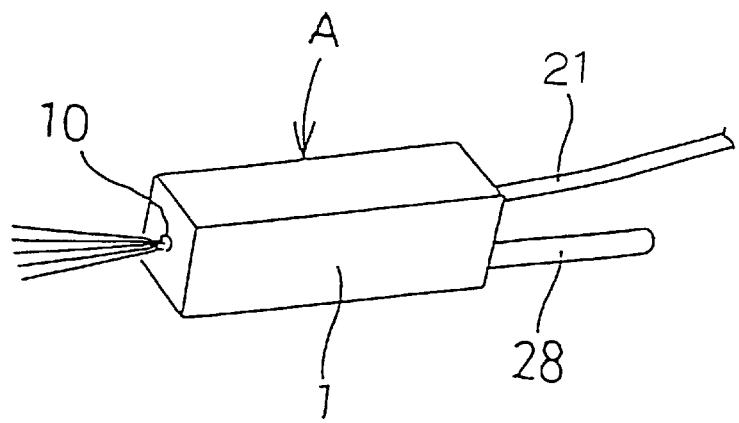
FIG. 11 is a perspective view showing a probe of a static electricity measuring system according to a third embodiment of the present invention.
Figure 12:
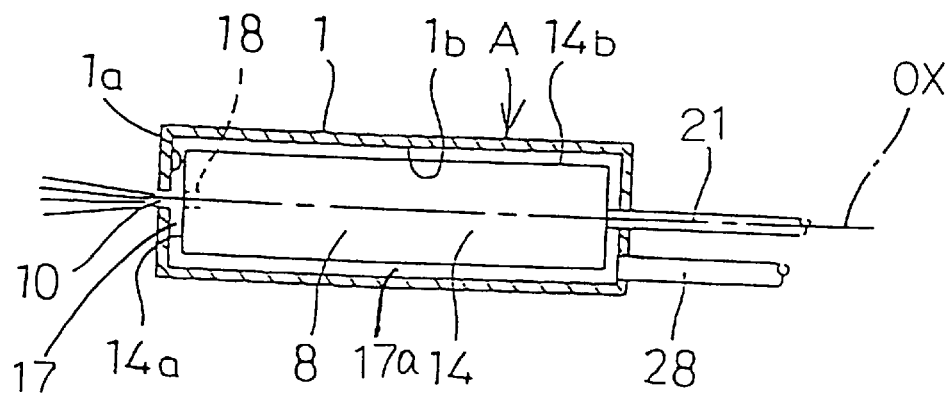
FIG. 12 is a cross-sectional view of the probe of the static electricity measuring system according to the third embodiment of the present invention.

FIGS. 11 and 12 illustrate a probe (A) according to a third embodiment of the present invention. The probe (A) includes a probe case 1 which has a rectangular parallelepiped shape and is made from, for example, metal. The probe case 1 contains a sensor 8 which includes a sensor case 14 having a rectangular parallelepiped shape and made from, for example, metal. Alternatively, the probe case 1 and the sensor case 14 may have a cylindrical shape. An air passage 17 is formed between a front outer surface 14a of the sensor case 14 and a front inner surface 1a of the probe case 1. An air passage 17a is formed between an inner circumferential surface 1b of the probe case 1 and an outer circumferential surface 14b of the sensor case 14. An air hose 28 is connected to the probe case 1 to communicate with the air passages 17a and 17. A purge hole 10 and a detecting hole 18 are positioned to have a common center axis OX. The cable 21 connects the static electricity detecting circuit in the sensor 8 to the measuring device (B) (see FIG. 2). In this embodiment, air is not supplied to the inside of the sensor 8.

The diameter of the purge hole 10 is, for example, approximately 1 to 5 mm. The electric field detecting sensitivity of the sensor 8 lowers as the diameter of the purge hole 10 reduces. In order to compensate the sensitivity of the sensor 8, the distance between the front outer surface 14a of the sensor case 14 and the front inner surface 1a of the probe case 1 is reduced. In this embodiment, the distance between the front outer surface 14a and the front inner surface 1a is, for example, about 1 mm. Further, the distance between the inner circumferential surface 1b of the probe case 1 and the outer circumferential surface 14b of the sensor case 14 is, for example, approximately 1 to 5 mm in order to reduce the size of the probe (A). Preferably, the purge hole 10 has a diameter as small as that of the detecting hole 18. Accordingly, the air discharged from the purge hole 10 has higher discharging speed.

Figure 13:
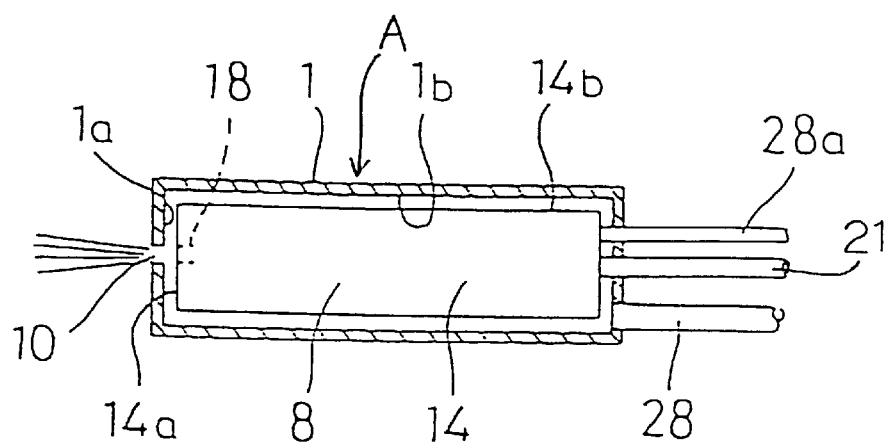
FIG. 13 is a cross-sectional view of a probe of a static electricity measuring system according to a fourth embodiment of the present invention.
Figure 14:
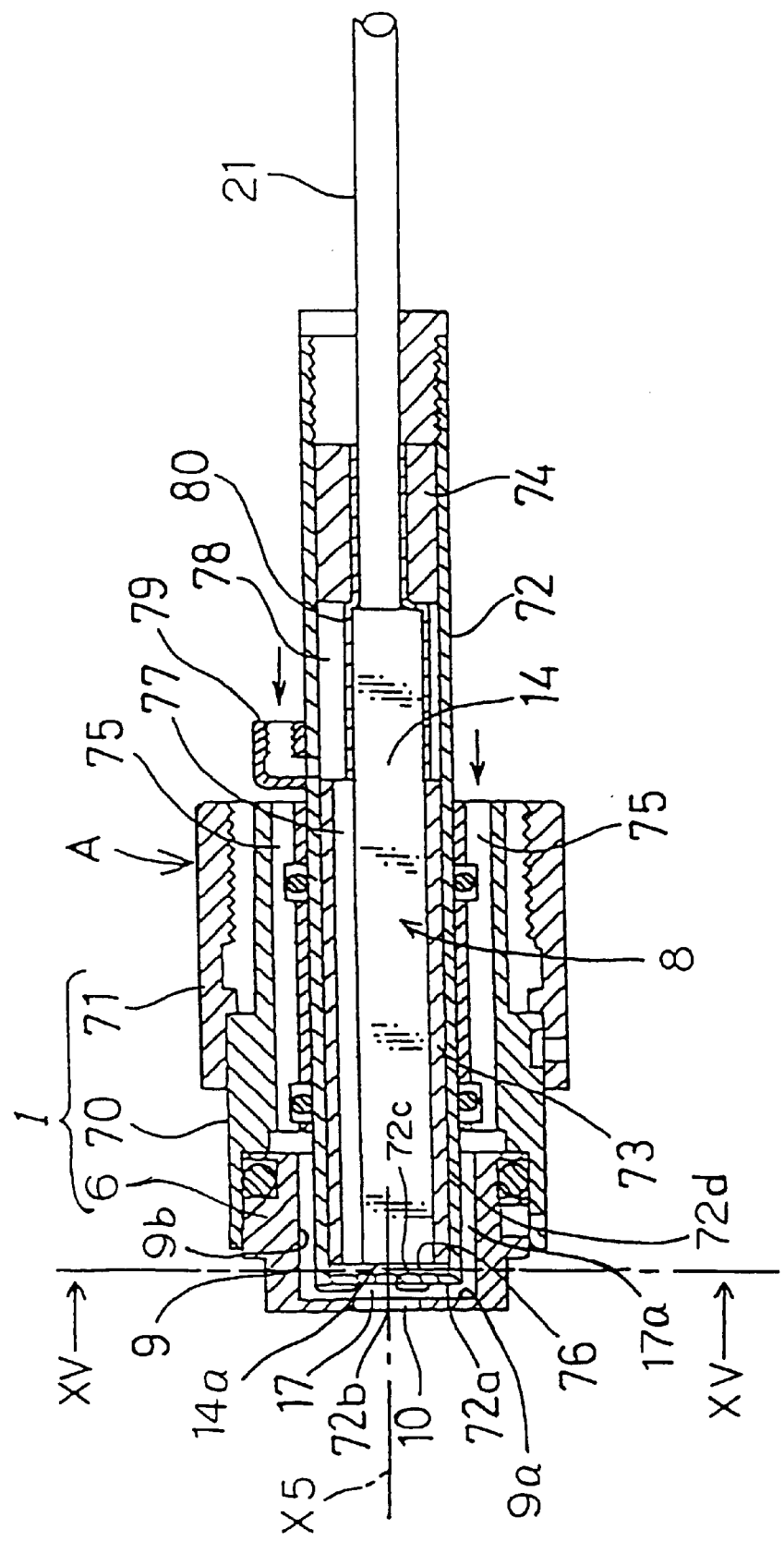
FIG. 14 is a cross-sectional view of a probe of a static electricity measuring system according to a fifth embodiment of the present invention.
Figure 15:
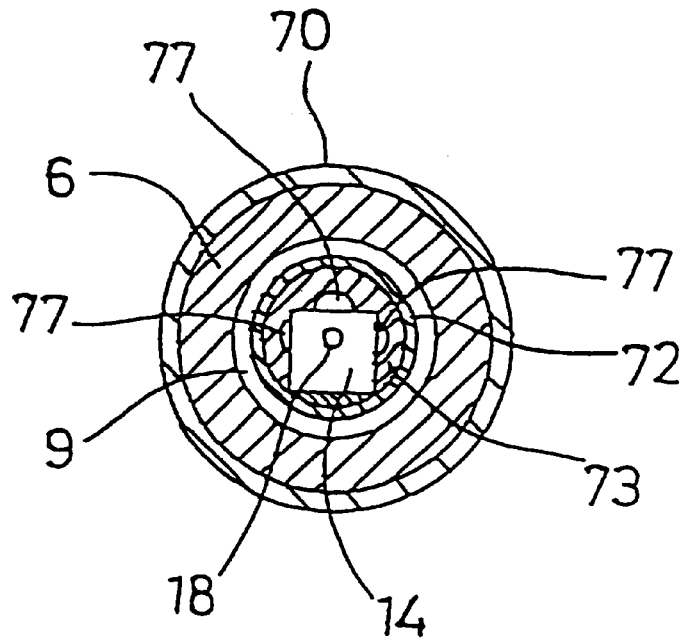
FIG. 15 is a cross-sectional view of the probe taken along a line XV—XV in FIG. 14.
Figure 16:
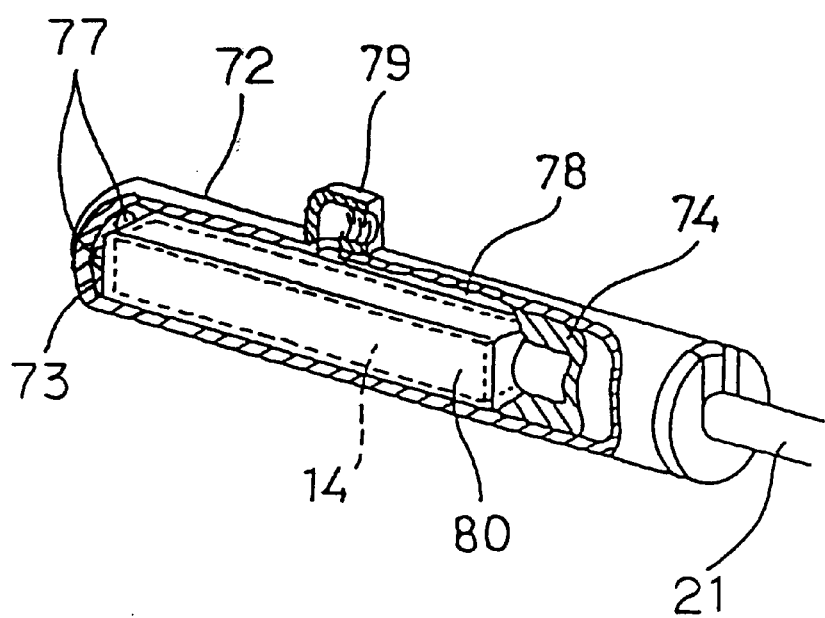
FIG. 16 is a partially cross-sectional perspective view of the probe of the static electricity measuring system according to the fifth embodiment of the present invention.
Figure 17:
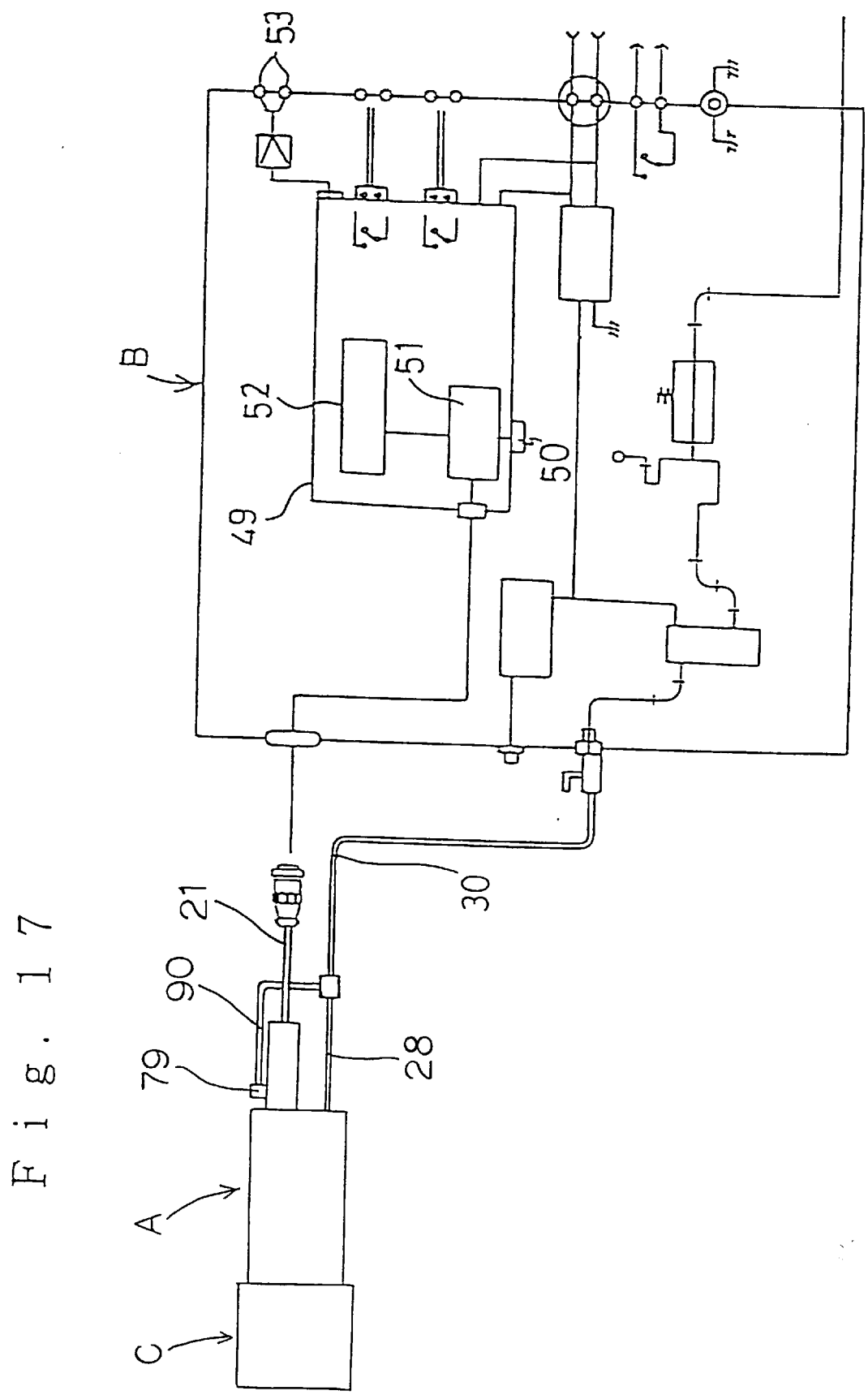
FIG. 17 illustrates a static electricity measuring system according to the fifth embodiment of the present invention.

FIG. 13 illustrates a probe (A) according to a fourth embodiment of the present invention. Referring to FIG. 13, the sensor case 14 is connected to an additional air hose 28a for supplying air inside the sensor case 14. Accordingly, since air is discharged from the detecting hole 18 of the sensor 8, particles and dust are prevented from entering the inside of the sensor 8.

FIGS. 14 to 17 show a fifth embodiment according to the present invention. Referring to FIGS. 14 to 17, a probe case 1 includes an outer cylinder 71; an inner cylinder 70 which is inserted into and connected to the outer cylinder 71; and a cylindrical front cap 6 which closes a front opening of the inner cylinder 70. A sensor 8 is contained in a sensor container 72 and is secured to the sensor container 72 using retaining cylinders 73 and 74 to form a gap 76 between an outer front surface 14a of the sensor case 14 and an inner front surface 72c of the sensor container 72. A sealing material 80 is provided between the sensor 8 and the retaining cylinders 74. The front portion of the sensor container 72 has a through hole 72b. The through hole 72b has a diameter of, for example, approximately 1 mm. The probe case 1 contains the sensor container 72 which encloses the sensor 8. The front cap 6 has a cylindrical concave portion 9 and a purge hole 10 which extends through the front cap 6 and communicates with the concave portion 9. The front cap 6, the cylindrical concave portion 9, and a purge hole 10 have a common center axis (X5). In this embodiment, the purge hole 10 has a diameter of, for example, approximately 1 mm and a length along the common center axis (X5) of, for example, about 1 mm. The front portion 72d of the sensor container 72 is arranged in the cylindrical concave portion 9 of the front cap 6 to form a gap 17 between the inner surface 9a of the concave portion 9 and a front surface 72a of the sensor container 72 and to form a gap 17a between an inner circumferential surface 9b of the concave portion 9 and an outer circumferential surface 72c of the sensor container 72. The inner cylinder 70 has plural passages 75 which communicate through the gaps 17a and 17. The rear ends of the plural passages 75 is connected to an air supplying tube 28 which are connected to the common air hose 30 (see FIG. 17). The sensor container 72 has plural passages 77 and passages 78. The passages 77 are formed between the outer circumferential surface of the sensor case 14 and the inner circumferential surface of the sensor container 72. The passages 78 connect the plural passages 77 to a nipple 79. The nipple 79 is connected to an air supplying tube 90 which is connected to the common air hose 30 (see FIG. 17). The sealing material 80 is also provided between the sensor case 14 and the retaining cylinder 74. The cable 21 connects the static electricity detecting circuit 122 (see FIG. 5) in the sensor 8 to the measuring device (B) (see FIG. 17).

Air is supplied to the plural passages 77 from the nipple 79, passes thorough the gap 76, and then is discharged from the through hole 72b and the purge hole 10. Further, air is supplied to the plural passages 75, passes thorough the gaps 17a and 17, and then is discharged from the purge hole 10. The discharging air pressure at the through hole 72b is higher than that at the air purge hole 10. Accordingly, air supplied to the gaps (17a and 17) does not enter the inside of the sensor container 72 through the through hole 72b.

In the present embodiment, an air purging effect can be obtained. Namely, particles and dust are prevented from entering the inside of the probe (A), because air is discharged from the air purge hole 10. Further, particles are prevented from adhering to the outside surface, especially, the front surface 72a of the sensor case 14, because the air supplied to the plural passages 77 is discharged from the through hole 72b after passing through the gap 76. Furthermore, since air is discharged from the through hole 72b of the sensor case 14, particles and dust are prevented from entering the inside of the sensor case 14. Still further, in this embodiment, the through hole 72b and the purge hole have small diameters enough to enhance the air purging effect.

If air is supplied to the inside of the sensor 8, detecting error of the electric field detected by the sensor 8 may increase as the amount of air supplied to the inside of the sensor 8 increases. Namely, static electricity cannot be precisely measured if enough air is supplied to the inside of the sensor 8 to obtain the air purging effect. In the present embodiment, air is not supplied to the inside of the sensor 8. Instead, the sensor 8 is contained in the sensor container 72 which is contained in the probe case 1, and air is supplied to an inner passage between the sensor 8 and the sensor container 72 and an outer passage between the sensor container 72 and the probe case 1. Accordingly, the sensor 8 can precisely detect the static electricity while particles and dust are prevented from entering the inside of the sensor case 14.

In this embodiment, the sensor container 72 is arranged in the probe case 1 such that the detecting hole 18 of the sensor 8 is positioned in the vicinity of the purge hole 10. Accordingly, even though the through hole 72b and the purge hole have small diameters enough to enhance the air purging effect, the sensor 8 can maintain its detecting performance.

Figure 18:
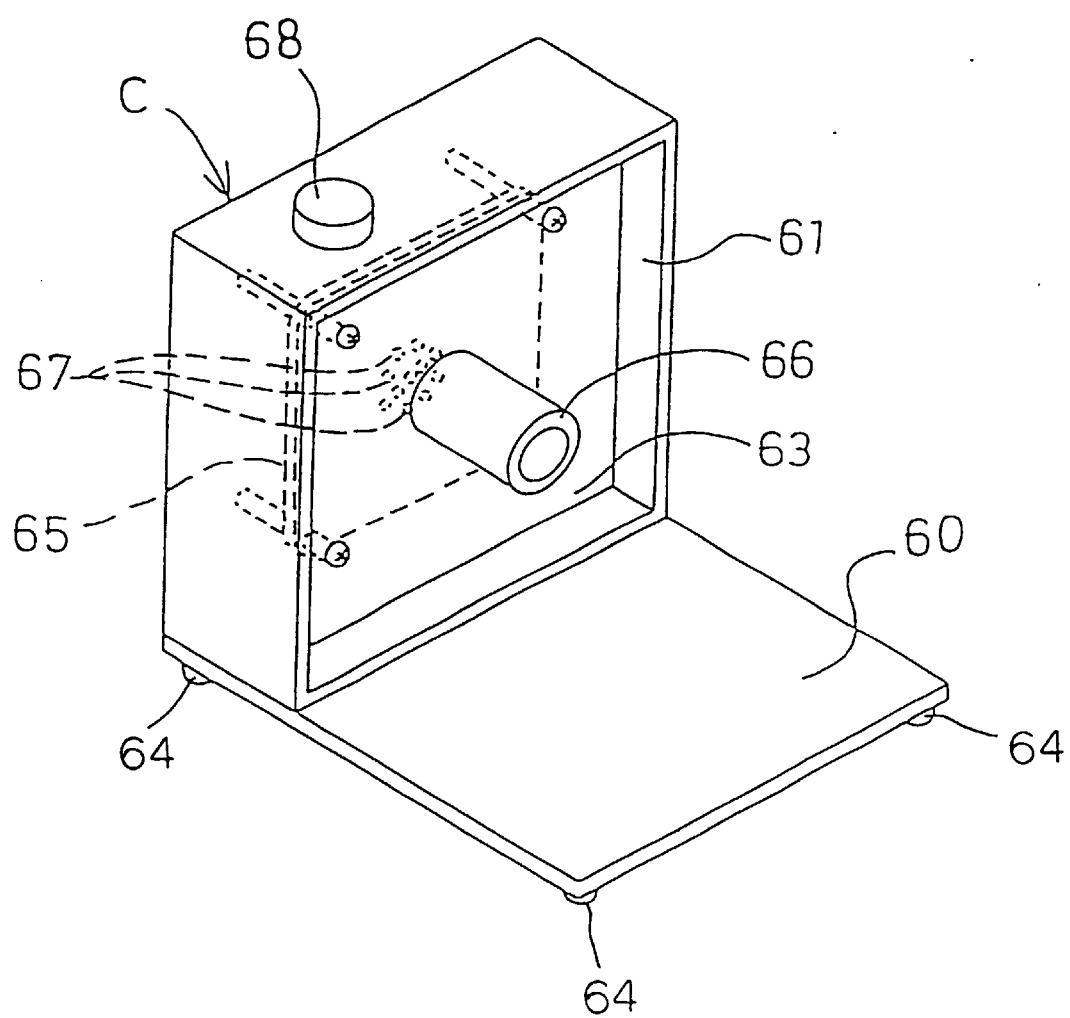
FIG. 18 is a perspective view of a calibration device of a static electricity measuring system according to a sixth embodiment of the present invention.
Figure 19:
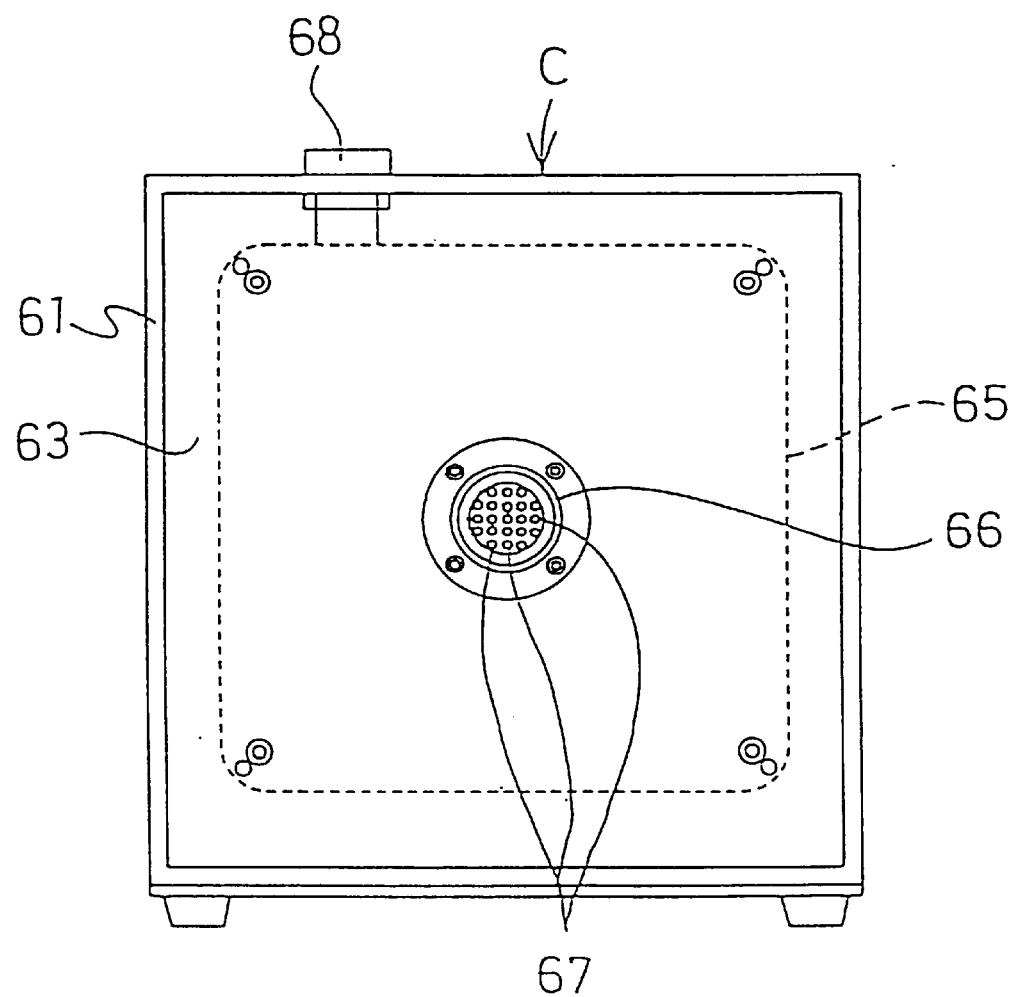
FIG. 19 is a side view of the calibration device of the static electricity measuring system according to the sixth embodiment of the present invention.
Figure 20:
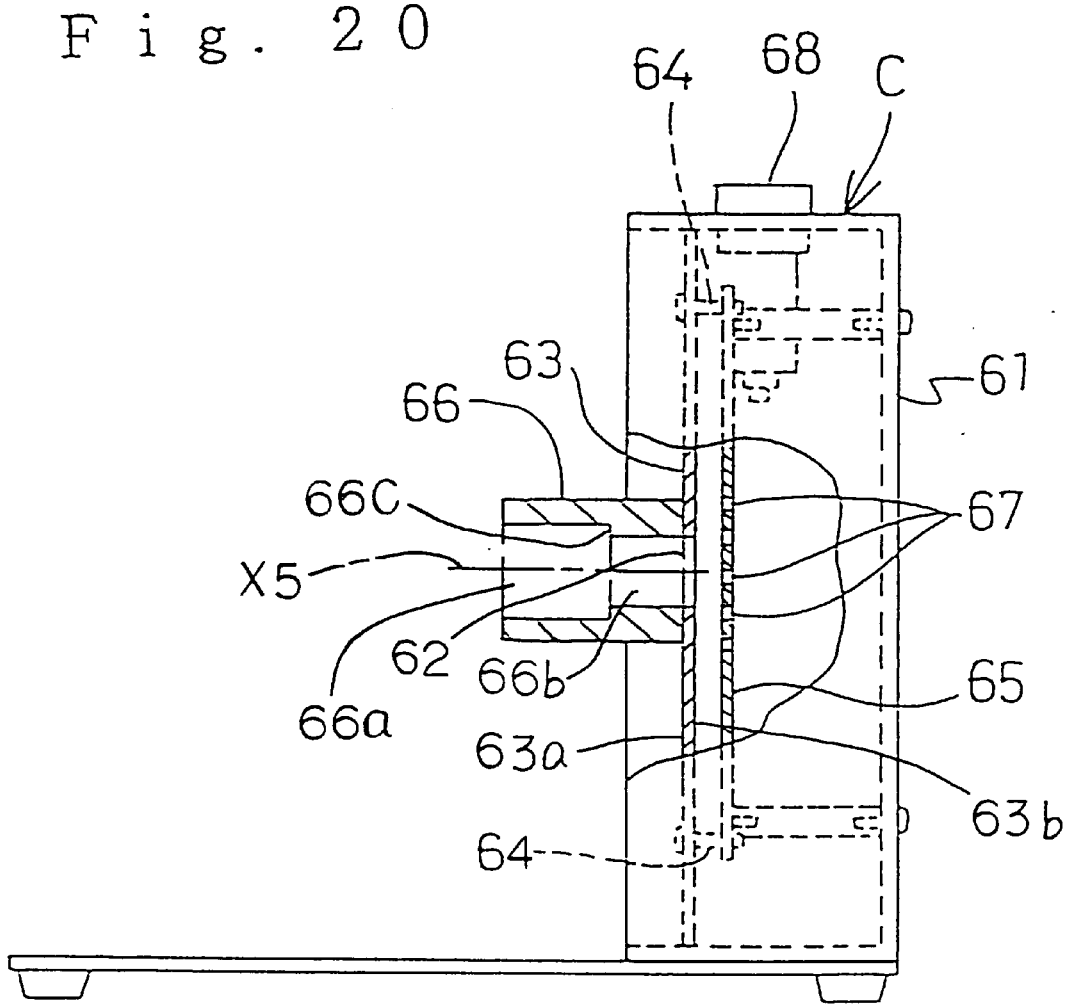
FIG. 20 is a cross-sectional view of the calibration device of the static electricity measuring system according to the sixth embodiment of the present invention.

FIGS. 18 to 20 illustrate a calibration device (C) according to a sixth embodiment of the present invention. Referring to FIGS. 18 to 20, the calibration device (C) includes a base plate 60 and a box-shaped frame 61 which is connected to the base plate 60. A support plate 63 is provided at the inside of the frame 61 to be substantially perpendicular to the base plate 60. The support plate 63 has a through hole 62 having a center axis X5 substantially perpendicular to the support plate 63 at the center of the support plate 63. A cylindrical holder 66 is provided on the front side 63a of the support plate 63 to have the center axis X5. A metal plate 65 is attached to the rear side 63b of the support plate 63 via spacers 64 to be in parallel with the support plate 63 and to be apart from the support plate 63. For example, the distance between the support plate 63 and the metal plate 65 is about 10 mm.

The metal plate 65 has plural small through holes 67 at the area corresponding to the through hole 62. The cylindrical holder 66 has a first cylindrical space 66a and a second cylindrical space 66b. The first cylindrical space 66a has a diameter slightly larger than that of the probe case 1 and the second cylindrical space 66b has a diameter smaller than that of the probe case 1. The first cylindrical space 66a is connected to the second cylindrical space 66b by a step portion 66c. The metal plate 65 is connected to a DC high-voltage power source (not shown) via a terminal 68.

When the measuring device (B) is adjusted, the front portion of the probe case 1 is inserted into the holder 66 to engage with the step portion 66c. DC high-voltage, for example, 10 KV is applied to the metal plate 65. In this calibration device (C), the measuring device (B) is adjusted while air is discharged from the air purge hole 10 because the metal plate 65 has plural through holes 67. Accordingly, the measuring device (B) can be adjusted more accurately.

Figure 21:
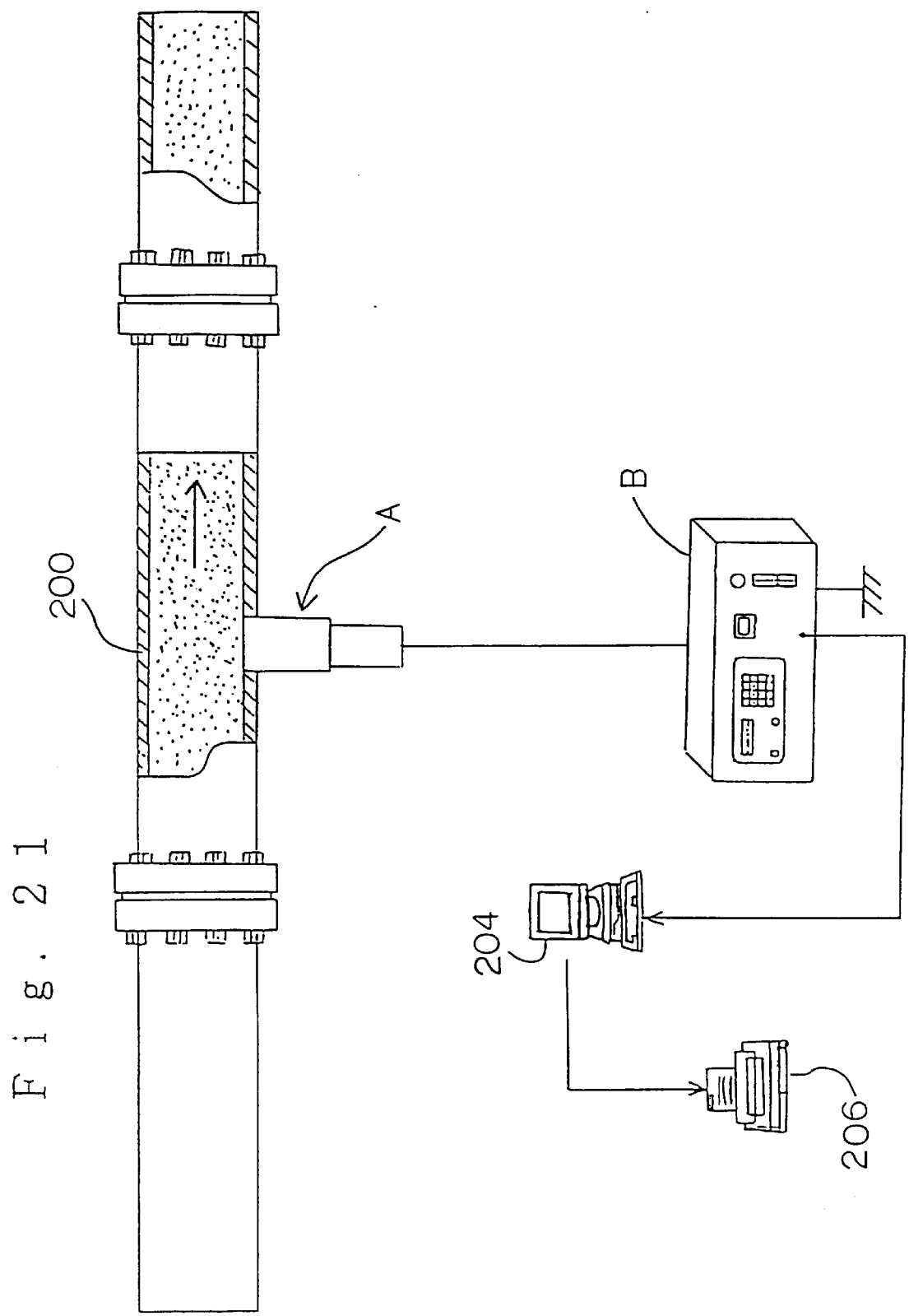
FIG. 21 shows a static electricity measuring apparatus of a static electricity measuring system according to the present invention which is attached to a powder pneumatic transportation system.

Although the static electricity measuring system is explained to measure static electricity of the particles which flow in the fluid dryer 100 (see FIG. 1), the system can be used to measure static electricity of the particles which flow in other apparatuses. For example, referring to FIG. 21, the system is applied to a powder pneumatic transportation system. In FIG. 21, a probe (A) is provided on a wall of a pipe 200 in which powder is transported by air along a direction shown by an arrow. The forward portion of the probe (A) is inserted in the pipe 200 through a hole provided in the pipe 200. The probe (A) is connected to a measuring device (B). The probe (A) detects static electricity of charged particles which flow inside the pipe 200. The measuring device (B) displays the detected static electricity and is connected to a computer 204 and a printer 206.

Although the static electricity measuring system is explained to measure static electricity of the powder in the above described embodiments, the present invention can be utilized to measure static electricity of other than powder, for example, mist, gas, vapor or the like.

Further, although air is supplied to the probe in the above described embodiments, other gases instead of air may be supplied to the probe. For example, inert gas such as nitrogen or argon can be supplied to the probe. Further, gas same as atmospheric gas which surrounds the probe can be supplied to the probe.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A static electricity measuring system comprising:
    a probe comprising:
        a sensor which is configured to detect an electric field and output signals representing the detected electric field;
        a probe case; and
        a sensor container which contains the sensor therein and which is contained in the probe case, the probe including a purge hole and at least one passage formed between the sensor container and the probe case, the purge hole being connected to the at least one passage, the sensor container including a detecting hole and at least one inner passage formed between the sensor and the sensor container, the detecting hole being connected to the at least one inner passage, the sensor being configured to detect the electric field through the purge hole and the detecting hole, gas being configured to be supplied to the at least one passage and the at least one inner passage and discharged from the purge hole and the detecting hole, respectively, the purge hole and the detecting hole having substantially a same diameter;
    a measuring device configured to measure static electricity on the basis of the signals output from the sensor; and
    a calibration device configured to generate a reference electric field, the measuring device being adjusted when the sensor detects the reference electric field produced by the calibration device.

2. A static electricity measuring system according to claim 1, wherein the purge hole and the detecting hole have a diameter of substantially 1 mm.

3. A static electricity measuring system according to claim 1, wherein the sensor container is arranged in the probe case such that the detecting hole is positioned facing the purge hole.

4. A static electricity measuring system according to claim 1, wherein the detecting hole has a length of substantially 1 mm.

5. A static electricity measuring system according to claim 1, wherein the gas comprises air.

6. A static electricity measuring system according to claim 1, wherein the probe case is made from metal.

7. A static electricity measuring system according to claim 1, wherein the sensor container is made from metal.

8. A static electricity measuring system according to claim 1, further comprising:
    a fluid dryer to which the probe is attached to measure static electricity of material flowing inside the fluid dryer.

9. A static electricity measuring system according to claim 1, wherein the calibration device includes a metal plate and a DC high-voltage generating circuit which generates the reference electric field.

10. A static electricity measuring system according to claim 9, wherein the sensor includes a detecting electrode and wherein the calibration device is attached to the probe such that the metal plate faces the electrode with a constant distance.

11. A static electricity measuring system according to claim 1, wherein the sensor includes a detecting electrode and wherein the calibration device includes a metal plate and a holder to support the probe such that the metal plate faces the electrode with a constant distance.

12. A static electricity measuring system according to claim 11, wherein gas is supplied to the inside of the probe, the metal plate having plural gas passing holes.

13. A static electricity measuring system according to claim 1, wherein the measuring device comprises a display which displays a value of an electric potential.

14. A static electricity measuring system according to claim 1, wherein the measuring device comprises a display which displays an electric charge.

15. A static electricity measuring system according to claim 1, wherein the calibration device is attached to the probe when the measuring device is adjusted and wherein the calibration device is detached from the probe when static electricity is measured.

16. A static electricity measuring system according to claim 1, further comprising:
a pneumatic transportation system to which the probe is attached to measure static electricity of material flowing inside the pneumatic transportation system.

17. A static electricity measuring system according to claim 1, wherein said electric field is electrostatic field.

18. A static electricity measuring system according to claim 1, wherein said reference electric field is reference electrostatic field.

19. A static electricity measuring system comprising:
a probe including a sensor which is configured to detect an electric field and output signals representing the detected electric field;
a measuring device configured to measure static electricity on the basis of the signals output from the sensor; and
a calibration device including a metal plate and a DC high-voltage generating circuit, the metal plate being configured to serve as an electromagnetic field radiator, the DC high-voltage generating circuit being configured to supply high-voltage to the metal plate so as to generate the reference electric field, the measuring device being adjusted while the sensor detects the reference electric field produced by the calibration device.

20. A static electricity measuring system according to claim 19, wherein the sensor includes a detecting electrode and wherein the calibration device is attached to the probe such that the metal plate faces the electrode with a constant distance.

21. A static electricity measuring system according to claim 19, wherein the sensor includes a detecting electrode and wherein the calibration device includes a metal plate and a holder to support the probe such that the metal plate faces the electrode with a constant distance.

22. A static electricity measuring system according to claim 21, wherein gas is supplied to the inside of the probe, the metal plate having plural gas passing holes.

23. A static electricity measuring system according to claim 19, wherein the probe has a case which includes at least one passage therein and a purge hole connected to the at least one passage, the sensor detecting the electric field through the purge hole when gas is supplied to the at least one passage and discharged from the purge hole.

24. A static electricity measuring system according to claim 23, wherein the at least one passage is provided between the case and the sensor.

25. A static electricity measuring system according to claim 23, wherein the sensor includes at least one additional passage therein and a detecting hole connected to the at least one additional passage, the sensor detecting the electric field through the detecting hole when the gas is supplied to the at least one additional passage and discharged from the detecting hole.

26. A static electricity measuring system according to claim 25, wherein a diameter of the detecting hole is smaller than that of the purge hole.

27. A static electricity measuring system according to claim 25, wherein the sensor is arranged in the probe such that the detecting hole is positioned facing the purge hole.

28. A static electricity measuring system according to claim 23, wherein the gas comprises air.

29. A static electricity measuring system according to claim 19, wherein the probe further comprises
a probe case, and
a sensor container which contains the sensor therein and which is contained in the probe case, the probe including a purge hole and at least one passage between the sensor container and the probe case, the purge hole being connected to the at least one passage, the sensor detecting the electric field through the purge hole, and gas is supplied to the at least one passage and discharged from the purge hole.

30. A static electricity measuring system according to claim 29, wherein the sensor container includes a detecting hole and at least one inner passage between the sensor and the sensor container, the detecting hole being connected to the at least one inner passage, the sensor detecting the electric field through the detecting hole, gas is supplied to the at least one inner passage and discharged from the detecting hole.

31. A static electricity measuring system according to claim 30, wherein the purge hole and the detecting hole have substantially a same diameter.

32. A static electricity measuring system according to claim 30, wherein the sensor has a detecting hole through which the sensor detects the electric field, and the sensor container is arranged in the probe case such that the detecting hole is positioned facing the purge hole.

33. A static electricity measuring system according to claim 19, wherein the probe includes a purge hole and the sensor includes a detecting hole, the sensor being positioned in the probe such that the detecting hole faces the purge hole.

34. A static electricity measuring system according to claim 19, further comprising:
a fluid dryer to which the probe is attached to measure static electricity of material flowing inside the fluid dryer.

35. A static electricity measuring system according to claim 19, wherein the measuring device comprises a display which displays a value of an electric potential.

36. A static electricity measuring system according to claim 19, wherein the calibration device is attached to the probe when the measuring device is adjusted and wherein the calibration device is detached from the probe when static electricity is measured.

37. A static electricity measuring system according to claim 19, further comprising:
a pneumatic transportation system to which the probe is attached to measure static electricity of material flowing inside the pneumatic transportation system.

* * * * *